United States Patent [19]
Barer et al.

[11] 3,931,165
[45] Jan. 6, 1976

[54] TRI-SUBSTITUTED TRIAZINES
[76] Inventors: Sol J. Barer, 18-01 Fox Run Drive, Plainsborough, N.J. 08536; Richard F. Stockel, 475 Rolling Hills Road, Bridgewater Township, N.J. 08876; Jaroslav Vit, 40 Partridge Run, Belle Mead, N.J. 08502
[22] Filed: May 2, 1974
[21] Appl. No.: 466,321

Related U.S. Application Data
[63] Continuation-in-part of Ser. No. 360,740, May 16, 1973, abandoned.

[52] U.S. Cl. .............. 260/249.8; 260/249.5; 71/93; 424/249
[51] Int. Cl.$^2$ ............... C07D 251/44; C07D 251/50
[58] Field of Search ....................... 260/249.5, 249.8

[56] References Cited
UNITED STATES PATENTS
B129,999  1/1975  Schwarzmann ................ 260/249.5

Primary Examiner—John M. Ford
Attorney, Agent, or Firm—Cushman, Darby & Cushman

[57] ABSTRACT
Novel halogenated triazines which are useful as insecticides, especially as herbicides.

19 Claims, No Drawings

TRI-SUBSTITUTED TRIAZINES

This application is a continuation-in-part of application Ser. No. 360,740 filed May 16, 1973 and now abandoned.

The present invention relates to novel triazines.

The compounds of the invention are N-halotriazines, preferably those in which the halo substituent has an atomic number of from 17 to 53 inclusive, and most preferably N-chlorotriazines of the formula (I):

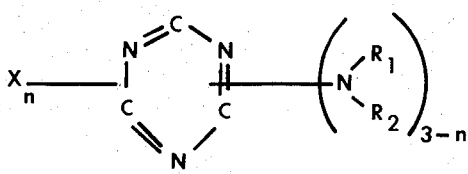

wherein $n$ is 1 or 2; wherein X is halogen; wherein $R_1$ is hydrogen, halogen, alkyl, alkenyl, cyanoalkyl, aralkyl, or cycloalkyl; wherein $R_2$ is alkyl, alkenyl, aralkyl, cycloalkyl, or Ar, the Ar variable being substituted or unsubstituted phenyl, diphenyl, naphthyl, or phenanthryl, the substituents on the substituted Ar variable being aliphatic hydrocarbon, aryl hydrocarbon, endo-aliphatic hydrocarbon, or halogen radicals; with the proviso that at least one $R_1$ is halogen. Preferably that halogen substituent is chlorine, and preferably $R_2$ is a hydrocarbon radical.

A further preferred group of compounds is the N-chlorotriazines having the formula (II):

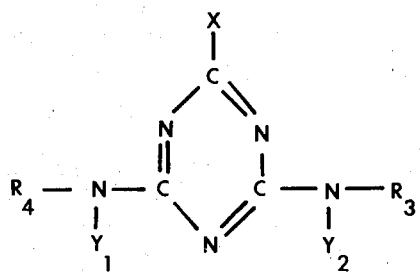

wherein $R_3$ and $R_4$, individually, are alkyl, preferably lower alkyl of 1 to 6 carbon atoms; wherein $Y_1$ is chlorine; and wherein $Y_2$ is hydrogen, alkyl, preferably lower alkyl of 1 to 6 carbon atoms, or chloro, and preferably still, $Y_2$ is lower alkyl of 1 to 6 carbon atoms or chloro.

The N-halotriazines are conveniently prepared by reacting a compound of Formula I in which at least one $R_1$ is hydrogen and neither $R_1$ nor $R_2$ is halogen, with a compound having the formula ROX wherein R is an alkyl or cycloalkyl group thereby replacing one or more of the amino hydrogen atoms of Formula I with X (halogen), the by-product being ROH. Illustrative ROX compounds include t-butyl hypochlorite, t-butyl hypobromite, t-butyl hypoiodite, t-amyl hypochlorite, 1-methylcyclopentyl hypochlorite, 1-methylcyclopentyl hypobromite, 1-methylcyclohexyl hypochlorite, n-propyl hypochlorite, isopropyl hypochlorite, ethyl hypochlorite, n-butyl hypochlorite, n-amyl hypochlorite, n-propyl hypobromite, n-hexyl hypochlorite, sec. butyl hypochlorite, and n-octyl hypochlorite. There can also be used inorganic hypohalites such as sodium hypochlorite, potassium hypochlorite, lithium hypochlorite, sodium hypobromite, sodium hypoiodite and calcium hypochlorite.

The preferred reaction procedure employs hypohalites of the formula ROX, preferably t-alkyl hypochlorites. The reaction is carried out conveniently at a temperature of about −30°C. to about +30°C. at atmospheric pressure in an inert organic medium, that is, inert under the reaction condition with the reactants and product. Illustrative inert organic media include esters such as methyl acetate, ethyl acetate, propyl acetate, methyl acetate, methyl pivalate, and butyl pivalate; halohydrocarbons, e.g., methylene chloride, carbon tetrachloride, chloroform, ethylene dichloride, trimethylene chloride, ethyl chloride, butyl chloride, isopropyl chloride, and anyl chloride; alcohols, e.g., methanol, ethanol, isopropanol, butanol, pentanol, hexanol, cyclohexanol, isooctyl alcohol, ethylene glycol, propylene glycol, trimethylene glycol, glycerine, diethylene glycol and dipropylene glycol. While operative temperatures above 30°C. can be employed, they are not preferred because of the tendency of the hypohalites to become unstable at elevated temperatures.

For agricultural purposes, for example, the novel N-halogenated triazines can be employed as a solution in the inert organic medium used in the process of making them. In fact, this is an obvious economic and application advantage since the corresponding compounds devoid of N-halogenation, e.g., 2-chloro-4,6-di(ethylamino) triazine (Simazine) and 2-chloro-4-ethylamino-6-isopropylaminotriazine (Atrazine) are quite insoluble in common organic diluents or solvents.

In preparing the novel halogenated triazines one equivalent of hypohalite is theoretically required for each amino jydrogen to be replaced by halogen. For example, to make compounds of Formula II from starting compounds wherein $Y_1$ is hydrogen and $Y_2$ is alkyl, at least one mole of t-butyl hypochlorite is required to make the N-monochlorinated triazine product. Less than 1 mole of t-butyl hypochlorite, e.g., 0.5 mole results in the formation of N-monochloro product in admixture with unreacted starting compound, e.g., 2-chloro-4,6-di(ethylamino)triazine. A moderate excess of t-butyl hypochlorite is desirably used, e.g., 1.5 to 4 equivalents, and higher, of hypochlorite per amino hydrogen contained in the reactant.

The compounds of the present invention are useful as herbicides, e.g., pre-emergent herbicides and post emergent herbicides, as fungicides, e.g., against *Alternaria oleraces*, *Fusarium*, *Pythium spp.*, *Helminthosporium salivum*, *lycopersici*, *Sclerolina fructicola*, *Alternaria solani*, as insecticides, e.g., against the house fly and flour beetles.

It should be understood that the novel halogenated triazines are halogenated 1,3,5-triazines.

Examples of compounds within the present invention are 2-chloro-4,6-di[(N-ethyl, N-chloro)amino]triazine, 2-chloro-4-(N-ethyl, N-chloro)amino-6-ethylaminotriazine, 2-chloro-4,6-di[(N-ethyl, N-bromo)amino]triazine, 2-chloro-4-[(n-ethyl, N-bromo)-amino]-6-ethylaminotriazine, 2-chloro-4,6-di[(N-ethyl, N-iodo)-amino]triazine, 2-chloro-4-(N-ethyl, N-iodo)amino-6-ethylaminotriazine, 2-bromo-4,6-di[(N-ethyl, N-chloro)amino]triazine, 2-bromo-4-(N-ethyl, N-chloro)amino-6-ethylaminotriazine, 2-iodo-4,6-di[(N-ethyl, N-chloro)amino]triazine, 2-iodo-4-(N-ethyl, N-chloroamino-6-ethylaminotriazine, 2-chloro-4-(N-ethyl, N-chloro)amino-6-(N-isopropyl, N- chloro)aminotriazine, 2-chloro-4-(N-ethyl, N-chloro)-amino-6-isopropylaminotriazine, 2-chloro-4-N-ethylamino-6-(N-isopropyl, N-chloro)triazine, 2-chloro-4,6-bis-[(N-methylbutyl, N-chloro)amino]triazine, 2-chloro-4-(N-methylbutyl, N-chloro)amino-6-methylbutylaminotriazine, 2-chloro-4,6-bis[(N-methyl, N-chloro)-amino]triazine, 2-chloro-4-(N-methyl, N-chloro)amino-6-methylaminotriazine, 2-chloro-4,6-bis[(N-hexyl, N-chloro)amino]triazine, 2-chloro-4-(N-hexyl, N-chloro)amino-6-hexylaminotriazine, 2-chloro-4,6-bis[(N-allyl, N-chloro)amino]triazine, 2-chloro-4-(N-allyl, N-chloro)amino-6-allylaminotriazine, 2-chloro-4-(N-methyl, N-chloro)amino-6-allylaminotriazine, 2-chloro-4,6-bis[(N-benzyl, N-chloro)amino]triazine, 2-chloro- 4-(N-benzyl, N-chloro)amino-6-benzylaminotriazine, 2-chloro-4,6-bis[(N-benzyl, N-bromo)-amino]triazine, 2-chloro-4,6-bis[(N-cyclohexyl, N-chloro)amino]-triazine, 2-chloro-4-(N-cyclohexyl, N-chloro)amino-6-cyclohexylaminotriazine, 2-chloro-4,6-bis[(N-isopropyl, N-chloro)amino]-triazine, 2-chloro-4-(N-isopropyl, N-chloro)amino-6-isopropylaminotriazine, 2-chloro-4,6-bis[(N-n-butyl, N-chloro)amino]-triazine, 2-chloro-4-(N-n-butyl, N-chloro)amino-n-butylaminotriazine, 2-chloro-4,6-bis[(N-t-butyl, N-chloro)amino]triazine, 2-chloro-4-(N-t-butyl, N-chloro)amino-6-t-butylaminotriazine, 2-chloro-4-(N-methyl, N-chloro)amino-6-diethylaminotriazine, 2-chloro-4-(N-methyl, N-chloro)amino-6-ethylaminotriazine, 2-chloro-4-(N-ethyl, N-chloro)amino-6-(N-n-propyl, N-chloro)-aminotriazine, 2-chloro-4,6-bis-[N-n-octyl, N-chloro)amino]-triazine, 2-chloro-4-(N-n-octyl, N-chloro)amino-6-(N-isooctyl, N-chloro)aminotriazine, 2-chloro-4-(N-n-octyl, N-chloro)amino-n-octylaminotriazine, 2-chloro-4-(N-methyl, N-chloro)amino-6-p-chlorophenylaminotriazine, 2-chloro-4-(N-ethyl, N-chloro)amino-6-(N-p-chlorophenyl, N-chloro)aminotriazine, 2-chloro-4,6-bis[(N-phenyl, N-chloro)amino]triazine, 2-chloro-4-(N-phenyl, N-chloro)-amino-6-anilinotriazine, 2-chloro-4,6-bis[(N-p-chlorophenyl, N-chloro)amino]triazine, 2-chloro-4-(N-p-chlorophenyl, N-chloro)-amino-6-p-chlorophenylaminotriazine, 2,4-dichloro-6-(N-methyl, N-chloro)aminotriazine, 2,4-dichloro-6-(N-ethyl, N-chloro)aminotriazine, 2,4-dibromo-6-(N-ethyl, N-chloro)aminotriazine, 2,4-dibromo-6-(N-ethyl, N-bromo)aminotriazine, 2,4-dichloro-6-(N-isopropyl, N-chloro)aminotriazine, 2,4-dichloro-(N-6-n-propyl, N-chloro)aminotriazine, 2,4-dichloro-6-(N-n-butyl, N-chloro)aminotriazine, 2,4-dichloro-(N-n-butyl, N-chloro)aminotriazine, 2,4-dichloro-6-(N-sec. butyl, N-chloro)aminotriazine, 2,4-dichloro-6-(N-hexyl, N-chloro)aminotriazine, 2,4-dichloro-6-(N-cyclohexyl-N-chloro)aminotriazine, 2,4-dichloro-6-(N-n-octyl, N-chloro)aminotriazine, 2,4-dichloro-6-(N-phenyl, N-chloro)aminotriazine, 2,4-dichloro- 6-(N-p-chlorophenyl, N-chloro)aminotriazine, 2,4-dichloro-6-(N-o-chlorophenyl, N-chloro)aminotriazine, 2,4-dichloro-6-(N-p-bromophenyl, N-chloro)aminotriazine, 2,4-dichloro-6-(N-chlorophenyl, N-bromo)aminotriazine, 2,4-dichloro-6-(N-m-chlorophenyl, N-chloro)aminotriazine, 2,4-dichloro-6-(N-benzyl, N-chloro)aminotriazine, 2,4-dichloro-6-(N-o-iodophenyl, N-chloro)amino-2,4-dichloro-6-(N-p-fluorophenyl, N-chloro)aminotriazine, 2,4-dichloro-6-(N-2′, 4′-dichlorophenyl, N-chloro)aminotriazine, 2-chloro-4-(N-p-fluorophenyl, N-chloro)amino-6-p-fluorophenylaminotriazine, 2,4-dichloro-6-(N-beta-naphthyl, N-chloro)aminotriazine, 2,4-dichloro-6-bis[(N-beta-naphthyl, N-chloro)amino]triazine, 2-chloro-4-(N-beta-naphthyl, N-chloro)amino-6-beta-naphthylaminotriazine, 2,4-dichloro-6-(N-9-phenanthryl, N-chloro)aminotriazine, 2,4-dichloro-6-(N-p-methylphenyl, N-chloro)aminotriazine, 2-chloro-4-(N-p-methylphenyl, N-chloro)amino-6-p-toluidinotriazine, 2,4-dichloro-6-(N-m-dodecylphenyl, N-chloro)aminotriazine, 2,4-dichloro-6-(N-dodecyl, N-chloro)aminotriazine, 2-chloro-4-(N-ethyl-N-chloroamino-6-dodecylaminotriazine, 2,4-dichloro-6-(N-o-ethylphenyl, N-chloro)aminotriazine, 2,4-dichloro-6-(N-p-phenylphenyl, N-chloro)aminotriazine, 2-chloro-4,6-bis (N-p-phenyl phenyl, N-chloro)aminotriazine, 2,4-dichloro-6-N-o-propenylphenyl, N-chloro)aminotriazine, p-chloro-4-(2,4-dimethylanilino-6-(N-phenyl, N-chloro)aminotriazine, 2-chloro-4-(N-chloro, N-ethyl)amino-6-[N-chloro, -N-(2-cyanoisopropyl)]-aminotriazine, 2-chloro, -4-(N-chloro, N-cyclopropyl)amino-6-(N-chloro, N-isopropyl)aminotriazine.

The triazine reactants used in the process to prepare the novel halogenated triazines can be those disclosed in Wolf U.S. Pat. No. 2,720,480 or Gysin U.S. Pat. No. 2,891,855. The entire disclosure of the Wolf and Gysin patents are hereby incorporated by reference. Examples of suitable starting triazines include 2-chloro-4,6-di(ethylamino)triazine, 2-bromo-4,6-di(ethylamino)-triazine, 2-iodo-4,6-di(ethylamino)triazine, 2-chloro-4-ethylamino-6-isopropylaminotriazine, 2-chloro-4,6-bis(methylbutylamino)triazine, 2-chloro-4,6-bis (methylamino)triazine, 2-chloro-4,6-bis(hexylamino)triazine, 2-chloro-4,6-bis(allylamino)triazine, 2-chloro-4-methylamino-6-allylaminotriazine, 2-chloro-4,6-bis(-benzylamino)-triazine, 2-chloro-4,6-bis(cyclohexylamino)triazine, 2-chloro-4,6-bis(isopropylamino)-triazine, 2-chloro-4,6-bis(n-butylamino)-triazine, 2-chloro-4,6-bis(t-butylamino)triazine, 2-chloro-4-methyl-6-diethylaminotriazine, 2-chloro-4-cyclopropyl-6-isopropyl-triazine, 2-chloro-4,6-bis(hexen-5-yl-amino)triazine, 2-chloro-4-methylamino-6-ethylaminotriazine, 2-chloro-4-ethylamino-6-n-propylaminotriazine, 2-chloro-4-ethylamino-6-2′-cyanoisopropyltriazine, 2-chloro-bis(n-octylamino)-triazine, 2-chloro-4-methylamino-6-p-chloroanilino-triazine, 2-chloro-4-ethyl-6-p-chloroanilinotriazine, 2-chloro-4,6-bis(anilino)triazine, 2-chloro-4,6-bis(p-chloroanilino)triazine, 2,4-dichloro-6-methylaminotriazine, 2,4-dichloro-6-ethylaminotriazine, 2,4-dibromo-6-ethylaminotriazine, 2,4-dichloro-6-isopropylaminotriazine, 2,4-dichloro-6-n-propylaminotriazine, 2,4-dichloro-6-n-butylaminotriazine, 2,4-dichloro-sec.butylaminotriazine, 2,4-dichloro-6-hexylaminotriazine, 2,4-dichloro-6-cyclohexylaminotriazine, 2,4-dichloro-6-n-octylaminotriazine, 2,4-dichloro-6-anilinotriazine, 2,4-dichloro-6-p-chloroanilinotriazine, 2,4-dichloro-6-o-chloroanilinotriazine, 2,4-dichloro-6-p-bromoanilinotriazine, 2,4-dichloro-6-m-chloroanilinotriazine, 2,4-dichloro-6-benzylaminotriazine, 2,4 -dichloro-6-o-iodoanilinotriazine, 2,4-dichloro-6-p-fluoroanilinotriazine, 2,4-dichloro-6-o,p-dichloroanilinotriazine, 2-chloro-4,6-bis-(p-fluoroanilino)triazine, 2,4-dichloro-6-beta-naphthylaminotriazine, 2-chloro-4,6-bis(beta-naphthylamino)triazine, 2,4-dichloro-6-(9-phenanthrylaminotriazine, 2,4-dichloro-6-toluidinotriazine, 2-chloro-4,6-bis(p-toluidino)triazine, 2,4-dichloro-6-m-dodecylanilinotriazine, 2,4-dichloro-6-dodecylaminotriazine, 2-chloro-4-ethylamino-6- dodecylaminotriazine, 2,4-dichloro-6-(o-ethylanilino)triazine, 2,4-dichloro-6-p-phenylanilinotriazine, 2-chloro-4,6-bis(p-phenylanilino)triazine, 2,4-dichloro-6-o-propenylanilinotriazine, and 2-chloro-4-o,p-dimethylanilino-6-anilinotriazine.

The novel N-chlorinated compounds of Formula I and especially those of Formula II have the aforementioned desired solubility in organic solvents.

The halogenated compounds of the invention can be employed as herbicides, fungicides, bactericides, and insecticides at widely varying rates, e.g., 0.1 to 100 lbs/acre, usually 1 to 30 lbs/acre. As foliar fungicides they are usually employed at a dosage of 0.1 to 20 lbs/acre. As insecticides they are normally used in a dosage of 0.2 to 10 lbs/acre. Of course, when the compounds are used as fungicides or insecticides on growing crops, e.g., wheat, cotton, barley, soybeans, corn, oats, turnips, tomatoes, beans, peas, carrots, broccoli, beets, trees, etc., they should not be used in an amount to kill the plants. The compounds also can be applied to seeds, or fabrics, etc., as fungicides, bactericides or insecticides. The compounds can also be used as defoliants and desiccants, e.g., for cotton by using them in less than lethal amounts.

The novel halogenated triazines for various agricultural applications as illustrated above are desirably employed admixed with inert solids to form dusts, powders, etc., or such triazines with/without such solids can be suspended in a suitable inert liquid diluent, e.g., comprising water, organic vehicle, etc. To such admixtures there can also be added surface active agents or wetting agents. The active ingredient can comprise from 0.01 to upwards of 50 weight percent and even upwards to 95 weight percent of the entire composition.

Illustrative inert liquid diluents include water and inert organic vehicles as carriers, e.g., hydrocarbons such as benzene, toluene, xylene, kerosene, diesel oil, fuel oil, and petroleum naphtha; ketones such as acetone, methyl ethyl ketone, and cyclohexanone; chlorinated hydrocarbons such as carbon tetrachloride, chloroform, trichloroethylene and perchloroethylene; esters such as ethyl acetate, amyl acetate and butyl acetate; alcohols; e.g., ethanol, methanol, isopropanol, amyl alcohol, ethylene glycol, propylene glycol, and glycerine. Mixtures of water and organic vehicle, either as solutions or emulsions, can be employed.

The novel compounds can also be applied as aerosols, e.g., by dispersing them in air by means of a compressed gas such as dichlorodifluoromethane or trichlorofluoromethane and similar halogenated alkanes.

In a partiuclar desirable embodiment, the novel halogenated triazines are admixed with or impregnated with or impregnated on various inert solid carriers which can be directly applied in the contemplated agricultural use, or they can be further admixed with an inert liquid diluent with/without additional ingredients, e.g., surface active agent, etc., and thereafter utilized in the cotemplated agricultural application. By the term "inert" is meant that the halogenated traizine and carrier and/or liquid diluent are substantially non-reactive towards each other. Additionally, it has been observed that various inert carriers are capable of enhancing the stability of the halogenated triazines over prolonged periods of time. For example, the alkali metal and alkaline earth metal borates, the precipitated hydrated silicon dioxides (HiSil1 404), hydrous calcium silicates such as those made by the hydrothermal reaction of diatomaceous earth, hydrated lime, and water (Microcel C and Microcel E), and the like.

The compounds of the present invention can also be applied with adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, tripoli, wood flour, walnut shell flour, redwood flour, and lignin.

Solid formulations comprising the novel halogenated triazine and inert carrier can be prepared in which the concentration of the ingredients vary over a considerably wide range, e.g., from about 5 to about 80 weight percent of said triazine based on the total weight of said triazine and said carrier. Optimum results and enhanced stability of the halogenated triazine have been observed using approximately 20 to 40 weight percent of said triazine based on the total weight of triazine and carrier.

As stated, it is oftentimes desirable to incorporate a surface active agent in the novel formulations comprising the novel halogenated triazines. Such surface active or wetting agents are advantageously employed in both the solid and liquid compositions. The surface active agent can be anionic, cationic or nonionic in character.

Typical classes of surface active agents include alkyl sulfonate salts, alkalaryl sulfonate salts, alkyl sulfate salts, alkylamine sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium salt of the sulfonated monoglyceride of cocoanut fatty acids, sorbitan sesquioleate, lauryl trimethyl ammonium chloride, octadecyl trimethyl ammonium chloride, polyethylene glycol lauryl ether, polyethylene esters of fatty acids and rosin acids, e.g., Ethofat 7 and 13, sodium N-methyl-N-oleyltaurate. Turkey Red oil, sodium dibutylnaphthalene sulfonate, sodium lignin sulfonate (Marasperse N) polyethylene glycol stearate, sodium dodecylbenzene sulfonate, tertiary dodecyl polyethylene glycol thioether (Nonionic 218), long chain ethylene oxidepropylene oxide condensation products, e.g., Pluronic 61 (molecular weight 1,000), sorbitan sesquioleate, polyethylene glycol ester of tall oil acids, sodium octyl phenoxyethyxyethyl sulfate, tris (polyoxyethylene) sorbitans monostearate (Tween 60), and sodium dihexyl sulfosuccinate.

The active ingredient per se or the active ingredient contained in a solution, dispersion, emulsion, suspension can be prepared via conventional techniques well known in the art.

The novel halogenated triazines or formulations containing same can also be admixed with hydrophilic polymers, either of the water soluble or the water insoluble type. Thus for controlled release of the herbicide, fungicide and insecticide of the present invention it can be entrapped in a hydrophilic polymer, e.g., in the form of a powder in the manner shown for medicines, flavors, fragrances, etc., in Shepherd U.S. Pat. No.

3,618,213. As hydrophilic polymers there can be used water insoluble polymers of water soluble hydroxyalkyl acrylates and methacrylates such as hydroxyethyl acrylate, hydroxypropyl acrylate, hydroxyethyl methacrylate, hydroxypropyl methacrylate, diethylene glycol monoacrylate, diethylene glycol monomethacrylate, dipropylene glycol monoacrylate, dipropylene glycol monomethacrylate or polymers of acrylamide, methacrylamide, vinyl pyrrolidone, and copolymers with polyethylenically unsaturated cross linking agents such as ethylene glycol dimethacrylate, ethylene glycol diacrylate, propylene glycol diacrylate, propylene glycol dimethacrylate, butylene dimethacrylate, divinyl benzene, triallyl melamine, N,N'-methylene bisacrylamide, pentaallyl sucrose, diallyl itaconate, allyl maleate, divinyl ether and others such as any of those set forth in Shepherd U.S. Pat. No. 3,575,123, col. 3, lines 15–35 for example. The cross linking agent can be present in an amount of 0.05% to 15% and upward to about 20%, usually 0.1 to 2.5% of the hydrophilic monomer.

There can also be included ethylenically unsaturated acids or salts thereof such as acrylic acid, cinnamic acid, methacrylic acid, itaconic acid, fumeric acid, maleic acid or partial esters such as 2-hydroxypropyl itaconate, 2-hydroxypropyl itaconate, 2-hydroxyethyl maleate, etc. There can also be used any of the other copolymerizable monomers set forth in the Shephers patent the entire disclosure of which is hereby incorporated by reference.

The novel compounds of the present invention can also be entrapped in water soluble hydrophillic homopolymers, e.g., hydrophilic polyacrylamide or polymethacrylamide, or water soluble copolymers of these materials with hydroxyethyl acrylate, hydroxyethyl methacrylate, hydroxypropyl acrylate, hydroxypropyl methacrylate, as well as any of water soluble hydrophilic copolymers set forth in Gould U.S. Pat No. 3,576,760, the entire disclosure of which is incorporated by reference. Thus the procedure of Gould Example 22 can be used replacing the 2,4 dichlorophenoxyacetic acid by one gram of 2-chloro-4-ethyl-N-chloroamino-6-isopropyl-N-chloroaminotriazine.

The novel halogenated triazines can also be incorporated in photodegradable polymers such as polyethylene, polypropylene, polybutene or copolymers such as ethylene-propylene copolymers which are applied as agricultural mulches and used in pesticidal applications, especially herbicidal applications. Typical examples of suitable photodegradable polymer compositions include those set forth in Shepherd U.S. Pat. No. 3,590,528, Newland U.S. Pat. No. 3,592,792, Field U.S. Pat. No. 3,341,357, Moore U.S. Pat. No. 3,320,695, Newland U.S. Pat. No. 3,454,570 and German Offenlegungsschrift 2,158,379.

Additionally, the pesticides can be admixed with biodegradable polymers e.g., thermoplastic polycaprolactones.

The pesticides of the present invention can be used in an amount of 0.1 to 10 weight percent, or even more, e.g., up to 50 weight percent, of such hydrophilic polymers, photodegradable polymers, and/or biodegradable polymers.

The following Examples are illustrative and are not to be considered as limiting the scope of the invention.

EXAMPLE 1

Preparation of 2-chloro-4,6-bis(N-chloro,N-ethylamino)-triazine

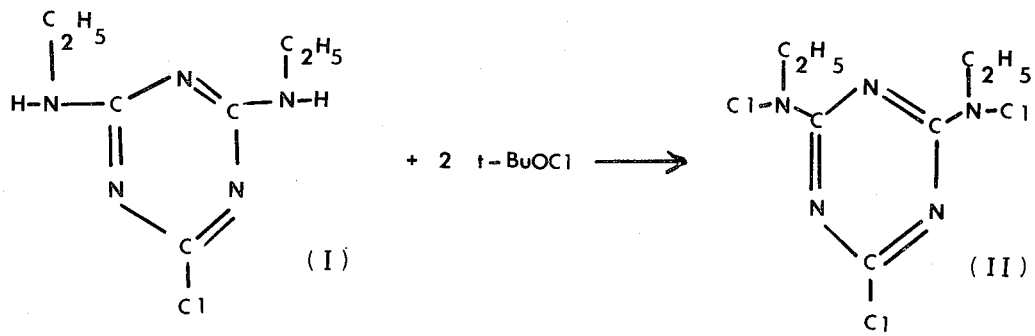

2-Chloro-4,6-bis(ethylamino)-s-triazine (Simazine), 200 grams (1 mole) was added to 1.5 liters of methanol. The resulting white suspension was cooled to 15°C. and 215 ml. (about 2 moles) of tert-butyl hypochlorite were added over a period of 15 minutes. A slight exotherm was observed. The reaction mixture was stirred for ½ hour at room temperature (about 22°C.). Thereafter the resulting homogeneous solution was stripped of methanol, tert-butanol and excess tert-butyl hypochlorite via vacuum distillation at room temperature. There was obtained 268 grams which was of a white solid identified as 2-chloro-4,6-bis(N-chloro,N-ethylamino)triazine.

Titration for active chlorine by $KI/Na_2 S_2O_3$ revealed 100% purity. The yield was 100%. Elemental analysis

| Found | | Theoretical | |
|---|---|---|---|
| C: | 31.54 | C: | 31.54 |
| H: | 3.80 | H: | 3.73 |
| N: | 25.85 | N: | 25.92 |
| Cl: | 39.00 | Cl: | 39.38 |

The infrared spectrum was consistent with structure (II), 2-chloro-4,6-bis(N-ethyl-N-chloroamino)-s-triazine.

In an analogous nammer, any of the compounds within Formula I, preferably within Formula II, can be prepared as disclosed in Example 1 above by replacing the starting 2-chloro-4,6-bis(ethylamino)triazine by the appropriate N-substituted-triazine and/or by changing the proportions of t-butyl hypochlorite to N-substituted-triazine and/or by replacing the t-butyl hypochlorite by another hypohalite or the formula a ROX described previously.

EXAMPLE 2

The procedure and proportions of Example 1 were employed except 230 grams (1 mole) of [2-chloro-4,6- bis(isopropylamino)-s-triazine], i.e., Propazine, was used. There was obtained 280 grams of an oil-like material which was further purified and identified above as 2-chloro-4,6-bis(N-isopropyl,N-chloroamino)-s-triazine.

EXAMPLE 3

The procedure and proportions of Example 1 were employed except 216 grams of [2-chloro,4-ethylamino-6-isopropylamino-s-triazine], i.e., Atrazine, was used. There was obtained 260 grams of an oil of 90% purity which was further purified and identified above as 2-chloro-4-N-chloroethyl-6-N-chloroisopropylamino-s-triazine.

EXAMPLE 4

Simazine (10 grams; 0.05 mole) was added to a mixture of 100ml. $CH_2Cl_2$ and 100ml of a 5 weight percent of aqueous solution of $Na_2CO_3$. The resulting suspension was stirred vigorously while chlorine gas bubbled therein. After approximately 15 minutes a clear two phase system formed. The organic ($CH_2Cl_2$) phase was separated, dried with $Na_2SO_4$, and stripped of solvent ($CH_2Cl_2$) in vacuo. An oil titrating as 100% N,N'-Dichlorosimazine was obtained which was further established by elemental analysis and by infrared analysis.

EXAMPLES 5-9

Five compounds were tested for herbicidal activity. These compounds are listed in Table I below.

TABLE I

| Compound 1 | 2-Chloro-4,6,-bis(N-chloro,N-ethyl)triazine |
| Compound 2 | Simazine |
| Compound 3 | Hexachloromelamine |
| Compound 4 | Trichloroisocyanuric acid |
| Compound 5 | t-Butyl hypochlorite |

Compound 1, i.e., 2-chloro-4,6-bis(N-ethyl,N-chloroamino)triazine, was formulated as a solution in methanol containing 1.0% volume/volume (v/v) of dimethylformamide. Simazine, i.e., 2-chloro-4,6-bis(ethylamino)triazine, was not sufficiently soluble in methanol and therefore had to be formulated in methanol containing 125 mg of Igepon AP 78 (coconut oil ester of sodium isethionate) as a wetting agent and 175 mg of Marasperse N-22 (sodium lignin sulfonate) as a dispersing agent per 15 ml of methanol. A spray volume of 15 ml was used with Compound 1 and 30 ml with Simazine since the latter was not sufficiently soluble to be prepared as a solution in 15 ml of methanol. Consequently, when the Simazine formulation was used the plants were sprayed twice to provide the same amounts of active ingredient.

Compound 3, Compound 4, and Compound 5 were also tested using the same formulation as for that of Compound 1. Formulation blanks were also applied in the herbicide tests. These blanks incuded no phytotoxicity in any of the tests.

Special precautions were taken to ensure that the time interval between formulating and spraying was kept to a minimum. This time interval did not exceed two minutes. All Compounds (1-5) were removed from the freezer, one at a time, weighed and formulated without delay.

Of Compounds 1-5 employed in the following herbicide tests, only Compound 1, that is, 2-chloro-4,6-bis(N-ethyl, N-chloroamino)triazine and Compound 2, i.e., Simazine were sufficiently active at 16 lbs/acre and were further tested at a lower rate of 4 lbs/acre.

Although the rating values for Compound 1 and Simazine are comparable at 16 lb/A, a striking difference was noted in the rate of development of toxicity. Phytotoxicity developed very slowly with Simazine, requiring a period of several days before any appreciable injury was observed. However, with Compound 1 severe phytotoxicity (necrosis and collapse of tissues) developed within several hours after treatment. The slow activity of Simazine may be due to poor foliar adsorption in contrast to better foliar adsorption for Compound 1. Much of the observed activity can probably be attributed to root uptake rather than foliar uptake of the Simazine.

With postemergence application Compounds 3 to 5 above, in addition to Compound 1, induced a high degree of contact injury in the form of necrosis and collapse of tissues. This degree of contact injury developed with striking rapidity following application to the subject plants, i.e., within several hours. However, for Compounds 3-5 the effect was not very persistent and many of the subject plants began to recover within several days. Grasses, in particular, because of their protected growing points, recovered rapidly. On the other hand, the degree of contact injury, to the subject plants when using Compound 1 was very severe and the subject plants failed to recover from their injured state. Commercial herbicides, in general, do not possess this characteristic.

With preemergence application at 16 lb/A. using Compounds 1-5, only Compound 1 and Simazine were sufficiently active to be retested at 4 lb/A. Compounds 3-5 were inactive or essentially inactivative as preemergence herbicides.

One aspect of triazine herbicides deserves discussion at this point. Triazines, in general, are relatively insoluble, in solvents normally used for formulation and application of agricultural chemicals. Consequently, these compounds in the past have been formulated as wettable powders. Unexpectedly and quite surprisingly, indeed, it was observed that many, if not substantially all, of the novel halogenated triazines can be formulated as water-soluble concentrates or emulsifiable concentrates. This characteristic imparts to the novel triazines obvious economic and application advantages.

The herbicidal evaluations were conducted in the following manner. Appropriate crop and weed species were seeded in individual 3 inch plastic pots (one unit). The seeds were covered with sand rather than soil to increase the sensitivity of preemergence testing (by reduced adsorption of chemicals on the soil). The soil depth was about 1.75 inches and the sand depth about 0.2 – 0.25 inch. For postemergence treatment the crop and weed species were seeded by growth-time requirement schedules and when the resulting plants had reached suitable growth development, generally the first true leaf stage, individual pots were selected for uniformity, Normally, a total of 12 crops and weeds were used in primary evaluation. A sandy loam soil type was used.

Unless otherwise indicated Compounds 1-5 were applied as sprays in a diluent volume of 50 gallons/acre. One carrying tray each of preemergence units and postemergence units was passed through the sprayer on a conveyor belt at about 1.5 miles per hour. As the tray passed through the sprayer it tripped a microswitch which in turn activated a solenoid valve and released the spray treatment. The sprayer was normally equipped with a Teejet 8003E nozzle tip and was operated in the range of 45 – 50 p. s. i. pressure. Compressed air was used as a driving force to apply pressure to the spray chamber.

Immediately after this treatment, preemergence and postemergence units were moved to the greenhouse and held for observation and ratings. The preemergence units were watered-in with a gentle surface spray several minutes after spray treatment using Compounds 1–5, a procedure shown to be effective in reducing loss of activity of volatile compounds.

Treated units were observed daily for imterim response. Final observations were made approximately 14 days after postemergence treatment and 21 days after preemergence treatment. Any treatments inducing questionable response were held beyond the 14 or 21 day observation period until such responses could be confirmed.

Observations included all abnormal physiological responses of stem bending, petiole curvature, epinasty, hyponasty, retardation, stimulation, root development, necrosis and related growth regulant characteristics.

Observations were reported as injury ratings, based on a scale of zero to ten (0 – 10), zero indicating no injury and ten indicating complete control.

Table II below contains the abbreviations used hereinafter (Tables IV–VI).

TABLE II

| Plant Species | | |
|---|---|---|
| Common Name | Botanical Name | Abbreviations |
| Bindweed | Convolvulus arvensis | BDWD |
| Cocklebur | Xanthium pensylvanicum | CKBR |
| Crabgrass | Digitaria sanguinalis | CBGS |
| Jimsonweed | Datura stramonium | JMWD |
| Johnsongrass (seed) | Sorghum halepense | JNGS(S) |
| Morningglory, Wild, Mixture of: | Ipomoea purpurea and I. hederacea | MNGY |
| Mustard | Brassica kaber | MSTD |
| Velvetleaf | Abutilon Theophrasti | VTLF |
| Watergrass | Echinochlor crusgalli | WRGS |
| Wild Oat | Avena fatua | WOAT |
| Yellow foxtail | Setaria glauca | YLFX |
| Yellow nutsedge (tubers) | Cyperus esculentus | YNSG(T) |

The code on plant injury and response is set forth in Table III below:

TABLE III

1. B REPRESENTS BURN
2. Cl REPRESENTS CHLOROSIS
3. Nc REPRESENTS NECROSIS
4. R REPRESENTS RETARDED OR REDUCED
5. P REPRESENTS PHYTOTOXIC

The preemergence and postemergence herbicide result at an application rate of 16 lbs/acre using Compounds 1–5 are set forth in Table IV.

EXAMPLES 10–12

In an analogous manner as described in Examples 5–9 above, Compound 1, Simazine, and Atrazine, i.e., 2-chloro-4-ethylamino-6-isopropylamino-s-triazine, were tested for preemergence and postemergence herbicidally activity using an application rate of 4 lbs/acre. The results are set out in Tables V and VI infra.

TABLE IV

HERBICIDE, PRE-EMERGENCE (INJURY RATING: PHYSIOLOGICAL RESPONSE)

| Cpd | Lb/A | YNSG(T) | OAT | JMWD | VTLF | JNGS(S) | BDWD | MSTD | YLFX | WRGS | CBGS | CKBR | MNGY | Days |
|---|---|---|---|---|---|---|---|---|---|---|---|---|---|---|
| 1 | 16 | 8:RNcCl | 10:Nc | 8:RNcCl | 10:Nc | 8:RNcCl | 7:RNcCl | 10:Nc | 9:Nc | 9:Nc | 10:Nc | 10:Nc | 10:Nc | 19 |
| 2 | 16 | 8:RNcCl | 10:Nc | 8:RNcCl | 9:Nc | 7:RCl | 2:Cl | 10:Nc | 9:Nc | 8:Nc | 10:Nc | 10:Nc | 10:Nc | 19 |
| 3 | 16 | 0:O | 0:O | 0:O | 0:O | 0:O | 0:O | 2:R | 0:O | 0:O | 0:O | 0:O | 0:O | 19 |
| 4 | 16 | 0:O | 0:O | 0:O | 0:O | 0:O | 0:O | 0:O | 0:O | 0:O | 0:O | 0:O | 0:O | 19 |
| 5 | 16 | 0:O | 0:O | 0:O | 0:O | 0:O | 0:O | 0:O | 0:O | 0:O | 0:O | 0:O | 0:O | 19 |

HERBICIDE, POST-EMERGENCE (INJURY RATING: PHYSIOLOGICAL RESPONSE)

| Cpd | Lb/A | YNSG(T) | OAT | JMWD | VTLF | JNGS(S) | BDWD | MSTD | YLFX | WRGS | CBGS | CKBR | MNGY | Days |
|---|---|---|---|---|---|---|---|---|---|---|---|---|---|---|
| 1 | 16 | 9:Nc | 10:Nc | 10:Nc | 10:NcCl | 10:Nc | 7:NcR | 10:Nc | 10:Nc | 10:Nc | 10:Nc | 10:Nc | 10:Nc | 12 |
| 2 | 16 | 9:NcCl | 10:Nc | 10:Nc | 9:Nc | 4:NcR | 9:Nc | 10:Nc | 10:Nc | 10:Nc | 10:Nc | 10:Nc | 10:Nc | 12 |
| 3 | 16 | 0:O | 2:Nc | 2:NcR | 1:Nc | 0:O | 0:O | 7:Nc | 2:Nc | 0:O | 2:Nc | 0:O | 1:Nc | 12 |
| 4 | 16 | 0:O | 1:Nc | 3:Nc | 1:Nc | 0:O | 0:O | 10:Nc | 0:O | 1:Nc | 1:Nc | 0:O | 1:Nc | 12 |
| 5 | 16 | 0:O | 2:Nc | 2:Nc | 1:Nc | 1:Nc | 0:O | 8:Nc | 0:O | 1:Nc | 4:Nc | 0:O | 1:Nc | 12 |

TABLE V

HERBICIDE (4 lb/acre), PREEMERGENCE (INJURY RATING: PHYSIOLOGICAL RESPONSE)

| Compound | Corn | Cotton | Soybean | YNSG(T) | WOAT | JMWD | VTLF | JNGS(S) |
|---|---|---|---|---|---|---|---|---|
| Compound 1 | 0:O | 5:Cl | 4:RCl | 7:NcClR | 8:NcCl | 5:ClR | 10:Nc | 7:NcCl |
| Atrazine | 0:O | 4:Cl | 8:Cl | 7:RCl | 9:Nc | 5:RCl | 10:Nc | 3:Cl |
| Simazine | 0:O | 3:Cl | 4:Cl | 6:RCl | 9:NcCl | 5:RCl | 10:Nc | 3:Cl |
| Compound 1 | 0:O | 10:Nc | 10:Nc | 10:Nc | 10:Nc | 10:Nc | 10:Nc | 8:NcClR |
| Atrazine | 0:O | 10:Nc | 10:Nc | 10:Nc | 10:Nc | 10:Nc | 10:Nc | 4:RCl |
| Simazine | 0:O | 10:Nc | 10:Nc | 10:Nc | 10:Nc | 10:Nc | 10:Nc | 9:NcCl |

| Compound | BDWD | MSTD | YLFX | BNGS | CBGS | CKBR | MNGY | Days |
|---|---|---|---|---|---|---|---|---|
| Compound 1 | 3:Cl | 10:Nc | 9:Cl | 9:RNcCl | 9:Nc | 8:NcCl | 10:Nc | 14 |
| Atrazine | 4:Cl | 9:Nc | 7:NcCl | 9:NcClR | 9:Nc | 5:RCl | 10:Nc | 14 |
| Simazine | 3:Cl | 9:Nc | 5:NcCl | 8:NcClR | 10:Nc | 3:Cl | 9:Nc | 14 |
| Compound 1 | 10:Nc | 10:Nc | 10:Nc | 10:Nc | 10:Nc | 10:Nc | 10:Nc | 21 |
| Atrazine | 10:Nc | 10:Nc | 10:Nc | 10:Nc | 10:Nc | 10:Nc | 10:Nc | 21 |
| Simazine | 10:Nc | 10:Nc | 10:Nc | 10:Nc | 10:Nc | 10:Nc | 10:Nc | 21 |

TABLE VI

HERBICIDE (4 lb/acre), POSTEMERGENCE
(INJURY RATING: PHYSIOLOGICAL RESPONSE)

| Compound | Corn | Cotton | Soybean | YNSG(T) | WOAT | JMWD | VTLF | JNGS(S) |
|---|---|---|---|---|---|---|---|---|
| Compound 1 | 1:Ne | 7:NeCl | 9:NeCl | 7:NeClR | 7:NeCl | 8:NeClR | 9:Ne | 7:NeClR |
| Atrazine | 0:O | 2:NeCl | 9:Ne | 5:R | 7:NeCl | 7:NeCl | 5:NeCl | 0:O |
| Simazine | 0:O | 1:Cl | 1:NeCl | 5:R | 6:NeCl | 6:NeCl | 7:NeCl | 0:O |
| Compound 1 | 0:O | 10:Ne | 10:Ne | 10:Ne | 10:Ne | 10:Ne | 10:Ne | 10:Ne |
| Atrazine | 0:O | 10:Ne | 10:Ne | 10:Ne | 10:Ne | 10:Ne | 10:Ne | 0:O |
| Simazine | 0:O | 10:Ne | 10:Ne | 9:NeCl | 10:Ne | 10:Ne | 10:Ne | 4:RCl |

| Compound | BDWD | MSTD | YLFX | BNGS | CBGS | CKBR | MNGY | Days |
|---|---|---|---|---|---|---|---|---|
| Compound 1 | 7:NeClR | 10:Ne | 9:Ne | 9:Ne | 9:Ne | 9:Ne | 8:NeCl | 5 |
| Atrazine | 4:ClR | 9:Ne | 8:NeCl | 9:Ne | 2:RCl | 5:NeCl | 9:Ne | 5 |
| Simazine | 6:NeClR | 9:NeCl | 9:Ne | 6:ClRNe | 0:O | 7:NeCl | 7:NeCl | 5 |
| Compound 1 | 10:Ne | 10:Ne | 10:Ne | 10:Ne | 10:Ne | 10:Ne | 10:Ne | 14 |
| Atrazine | 10:Ne | 10:Ne | 10:Ne | 10:Ne | 0:O | 10:Ne | 10:Ne | 14 |
| Simazine | 10:Ne | 10:Ne | 10:Ne | 10:Ne | 7:RNe | 10:Ne | 10:Ne | 14 |

EXAMPLES 13–17

Compounds 1–5 were also tested as insecticides, insect growth regulants, and foliar fungicides. Compound 1 showed moderate control of Tobacco Mosaic Virus. It also shows 60% mortality of adult mites but was not residually active against emerging young at the rate tested. In attempted nemotocide tests Compound 1 was phytotoxic to the tomato host plant at a rate of 100 lbs/acre.

Table VII below contains the abbreviations used hereinafter (Tables VIII–XI).

TABLE VII

| | | |
|---|---|---|
| 1. | DW | is Deionized Water |
| 2. | TB | is 3% tertiary butanol solution |
| 3. | WP | is wettable powder |
| 4. | MI | is Marasperse AP 78 and Igepon N-22 in dionized water solution |
| 5. | SAW-SP | is Seven Army worm - stomach poison |
| 6. | BW-B | is Boll Weevil - bait test |
| 7. | HF-B | is Housefly - bait test |
| 8. | TSM-C | is two spotted spider mite - contact test |
| 9. | TSM-O | is two spotted spider mite - ovicidal test |
| 10. | PS-SSD | is Pea Aphid - soil drench test |
| 11. | YFM-IV | is Yellow Fever Mosquito larvae - in vitro |
| 12. | YMW-MT | is yellow mealworm - modified topical test |
| 13. | MBB-MT | is Mexican bean beetle - modified topical test |
| 14. | BW-MT | is boll weevil - modified topical test |
| 15. | HF-MT | is house fly - modified topical test |
| 16. | MWB-MT | is Milkweed Bug - modified topical test |
| 17. | LBT | is Late Blight of Tomatoes (*Phytophthora infestans*) |
| 18. | RBD | is Rice Blast Disease (*Pyricularia oryzae*) |
| 19. | PMC | is powdery mildew of cucumber (*Erysiphe cichoracearum*) |
| 20. | LRW | is Leaf Rust of Wheat (*Puccinia recondita tritici*) |
| 21. | BLT | is Bacterial Leaf Spot of Tomatoes (*Xanthomonas vesicatoria*) |
| 22. | TMV | is Tobacco Mosaic Virus |
| 23. | EBT | is Early Blight of Tomatoes (*Alternaria solani*) |

Tables VIII, IX, X, and XI below set out the results using Compounds 1–5 as insecticides, as insect growth regulants, as protectant foliar fungicides, and as systemic fungicides.

TABLE VIII

Insecticidal-Miticidal Efficacy
% Mortality: Response

| Compound | Formulation | Conc. ppm | SAW-SP | BW-B | HF-B | TSM-C | TSM-O | PA-SSD | YFM-T |
|---|---|---|---|---|---|---|---|---|---|
| 1 | WP | 2400 | 10:0 | 0:0 | 12:0 | 60:0 | 0:P2 | | |
| | | 100 | | | | | | 0:0 | 100:0 |
| 2 | MI | 2400 | 0:0 | 0:0 | 20:0 | 0:0 | 0:P1 | | |
| | | 100 | | | | | | 0:0 | 50:0 |
| 3 | WP | 2400 | 0:0 | 0:0 | 40:0 | 0:0 | 0:P1 | | |
| | | 100 | | | | | | 0:0 | 100:0 |
| 4 | WP | 2400 | 0:0 | 0:0 | 0:0 | 0:0 | 0:0 | | |
| | | 100 | | | | | | 0:0 | 0:0 |
| 5 | DW | 2400 | 0:0 | 0:0 | 0:0 | 0:0 | 0:P1 | | |
| | | 100 | | | | | | 0:0 | 90:0 |

In response P1 means trace phylotoxicity
P2 means slight phylotoxicity (plants recover, no reduction in growth)
0 means no injury

TABLE IX

Insect Growth Regulant Responses

| Compound | Formulation | Conc. ppm | YMW-MT | MBB-MT | BW-MT | HF-MT | MWB-MT | YFM-IV |
|---|---|---|---|---|---|---|---|---|
| 1 | WP | 2400 | 0:0 | 0:0 | 100:10 | 0:0 | 95:8.4 | |
| | | 100 | | | | | | 100:10 |
| 2 | MI | 2400 | 0:0 | 0:0 | 90:10.4 | 0:0 | 10:4 | |
| | | 100 | | | | | | 0:0 |
| 3 | WP | 2400 | 0:0 | 0:0 | 0:0 | 0:0 | 0:0 | |
| | | 100 | | | | | | 100:0 |
| 4 | WP | 2400 | 0:0 | 0:0 | 0:0 | 0:0 | 0:0 | |
| | | 100 | | | | | | 0:0 |
| 5 | DW | 2400 | 0:0 | 100:5.2 | 0:0 | 0:0 | 30:4 | |
| | | 100 | | | | | | 100:10 |

In response 0 means no injury
10 means plants dead

TABLE X

Protectant Foliar Fungicidal Efficacy
% Disease Control: Plant Injury (0–10 scale)

| Compound | Conc. ppm | LBT | RBD | PMC | LRW | BLT | TMV |
|---|---|---|---|---|---|---|---|
| 1 | 2000 | P:10B | O:8B | P:10B | 100:5B | P:10B | |
| | 1000 | | | | | | 90:0 |
| 2 | 2000 | P:10B | P:10B | P:10B | 100:6B | P:10B | |
| | 1000 | | | | | | 44:0 |
| 3 | 2000 | 57:2B | 97:5B | P:10B | 100:1B | 64:6B | |
| | 1000 | | | | | | 79:0 |
| 4 | 2000 | 71:1B | 93:4B | 0:1B | 100:0 | P:9B | |
| | 1000 | | | | | | 0:0 |
| 5 | 2000 | 2:0 | 0:0 | 0:0 | 0:0 | 29:0 | |
| | 1000 | | | | | | 0:0 |

B means burn

TABLE XI

SYSTEMIC FUNGICIDAL EFFICACY
Disease Control:
Plant Injury (1–10 Scale)

| Compound | Lbs per Acre | PMC | LRW | EBT |
|---|---|---|---|---|
| 1 | 40 | P:10 | 100:5 | 0:2 |
| 2 | 40 | P:10 | 100:5 | 0:1 |
| 3 | 40 | 0:4 | 0:1 | 0:0 |
| 4 | 40 | 0:3 | 0:0 | 57:0 |
| 5 | 40 | 0:0 | 0:0 | 0:0 |
| No reference standard available for early blight of tomatoes | | | | |
| Inoculated controls (1) | | 100 | 269 | 332 |

(1): Inoculated controls expressed as:
PMC: Percent leaf area diseased
LRW: Average number of infection loci per plant based on 3 replicates
EBT: Average number of infection loci per plant based on 3 replicates An example of a photodegradable composition is 100 parts of polybutene, 0.05 part of di-t-butyl-p-cresol, and 10 parts of Compound 1. This composition can be formed into a film, then applied to a field of corn, and thereafter it disintegrates.

In lieu of Compound 1, there can be employed other novel halogenated triazines having the Formula I, preferably Formula II, in the agricultural evaluation described in the preceding Examples and Tables.

What is claimed is:

1. A compound having the formula:

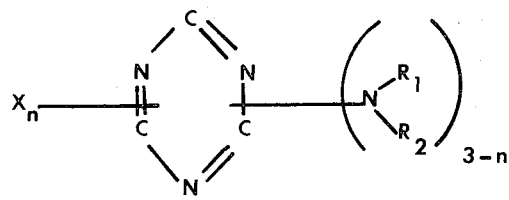

wherein $n$ is 1 or 2; wherein X is a halogen; wherein $R_1$ is hydrogen, halogen, alkyl of 1 to 12 carbon atoms, allyl, benzyl, cyclopropyl or cyclohexyl; wherein $R_2$ is alkyl of 1 to 12 carbon atoms, allyl, cyanoisopropyl, benzyl, cyclopropyl, cyclohexyl, phenyl, halophenyl, methylphenyl, ethylphenyl, propenylphenyl, diphenyl, naphthyl or phenanthryl, with the proviso that at least one $R_1$ is halogen.

2. A compound according to claim 1 wherein X is halogen having an atomic number of from 17 to 53, and wherein all $R_1$ halogen atoms have an atomic number of from 17 to 53.

3. A compound according to claim 2 wherein X is chlorine and wherein all $R_1$ halogen atoms are chlorine.

4. A compound according to claim 2 wherein $R_1$ is hydrogen, halogen of atomic number of from 17 to 53 or alkyl of 1 to 12 carbon atoms; and wherein $R_2$ is alkyl of 1 to 12 carbon atoms.

5. A compound according to claim 4 wherein $n$ is 2.

6. A compound according to claim 4 wherein $n$ is 1.

7. A compound according to claim 1 having the formula:

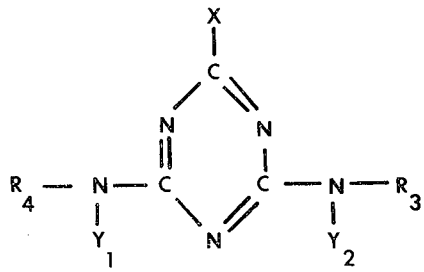

wherein $R_3$ and $R_4$ individually are alkyl of 1 to 12 carbon atoms; wherein X is a halogen; wherein $Y_1$ is halogen; and $Y_2$ is hydrogen, alkyl of 1 to 12 carbon atoms, or halogen.

8. A compound according to claim 7 wherein X and Y, individually, are halogen of atomic number of from 17 to 53; and wherein $Y_2$ is hydrogen or halogen of atomic number of from 17 to 53.

9. A compound according to claim 8 wherein all halogen atoms are chlorine.

10. A compound according to claim 9 wherein $R_3$ and $R_4$ are lower alkyl groups of 1 to 6 carbon atoms.

11. A compound according to claim 10 wherein $R_3$ and $R_4$ are both ethyl.

12. A compound according to claim 10 wherein $R_3$ is ethyl and wherein $R_4$ is isopropyl.

13. A process of preparing a compound according to claim 1 comprising reacting a hypohalite of the formula ROX or Ca(OX)$_2$ where R is sodium, potassium, lithium, 1 to 8 carbon atom alkyl, methylcyclopentyl or methycyclohexyl hypohalite with a triazine of the formula:

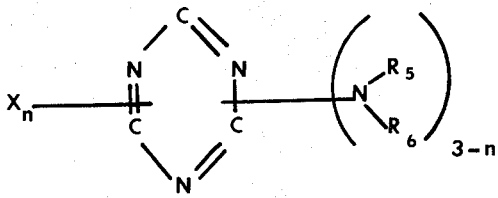

wherein $n$ is 1 or 2; wherein X is a halogen, wherein $R_5$ is hydrogen, alkyl of 1 to 12 carbon atoms, allyl, benzyl, cyclopropyl or cyclohexyl and wherein $R_6$ is alkyl of 1 to 12 carbon atoms, allyl, benzyl, cyclopropyl, cyclohexyl, phenyl, halophenyl, methyphenyl, ethylphenyl, propenylphenyl, diphenyl, naphthyl or phenanthryl.

14. A process according to claim 13 wherein the hypohalite has the formula $R_7$OX wherein $R_7$ is alkyl of 1 to 8 carbon atoms, methylcyclopentyl or methylcyclohexyl.

15. A process according to claim 14 wherein $R_7$ is tertiary alkyl.

16. A process according to claim 15 wherein $R_7$OX is t-butyl hypochlorite.

17. A process according to claim 16 wherein the reaction is carried out in an inert organic medium.

18. A process according to claim 17 wherein the temperature is −30 to +30°C.

19. A process according to claim 13 wherein the temperature is −30 to +30°C.

* * * * *